United States Patent
Brugmans et al.

(10) Patent No.: US 11,851,669 B2
(45) Date of Patent: *Dec. 26, 2023

(54) MAIZE PLANTS WITH IMPROVED DISEASE RESISTANCE

(71) Applicant: Seminis Vegetable Seeds, Inc., St. Louis, MO (US)

(72) Inventors: Bart Willem Brugmans, Beek en Donk (NL); Jonathan Tyler Eckard, Richmond, CA (US); David Elon Fisher, Waunakee, WI (US); Tim J. Gustafson, Sun Prairie, WI (US); Chad Kramer, Winters, CA (US)

(73) Assignee: SEMINIS VEGETABLE SEEDS, INC., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/068,525

(22) Filed: Oct. 12, 2020

(65) Prior Publication Data

US 2021/0087578 A1 Mar. 25, 2021

Related U.S. Application Data

(63) Continuation of application No. 16/145,987, filed on Sep. 28, 2018, now Pat. No. 10,858,668.

(60) Provisional application No. 62/566,305, filed on Sep. 29, 2017.

(51) Int. Cl.
  *C12N 15/82* (2006.01)
  *A01H 6/46* (2018.01)

(52) U.S. Cl.
  CPC ....... *C12N 15/8282* (2013.01); *A01H 6/4684* (2018.05)

(58) Field of Classification Search
  CPC .................................................. C12N 15/8282
  USPC ......................................................... 800/279
  See application file for complete search history.

(56) References Cited

U.S. PATENT DOCUMENTS 9,743,616 B1  8/2017  Orebaugh et al.
10,858,668 B2 * 12/2020  Brugmans ............ C12Q 1/6895

2015/0376644 A1  12/2015  Li et al.
2016/0201080 A1  7/2016  Ouzunova et al.
2017/0172098 A1  6/2017  Bourdoncle et al.

FOREIGN PATENT DOCUMENTS

DE  102013014637  3/2015
WO  2011/163590   12/2011
WO  2016/022517   3/2015

OTHER PUBLICATIONS

Carson et al. Plant Disease, (79) 717-720 (Year: 1995).*
Chung, et al., Characterization and fine-mapping of a resistance locus for northern leaf blight in maize bin 8.06, Theor. Appl. Genetics 121:205-227, 2010.
Extended European Search Report and Written Opinion regarding European Application No. 18863392.9, dated Jun. 7, 2021.
Carson, "A New Gene in Maize Conferring the 'Chlorotic Halo' Reaction to Infection by Exserohilum turcicum," Plant Disease 79(7):717-720 (1995).
Hurni, et al., "The Maize Disease Resistance Gene Htn1 Against Northern Corn Leaf Blight Encodes a Wall-Associated Receptor-Like Kinase," Proceedings of the National Academy of Sciences for the United States of America 112(28):8780-8785 (2015).
International Search Report and Written Opinion for PCT/US2018/053419, dated Jan. 15, 2019.
Van Inghelandt, et al., "Genome-Wide Association Mapping of Flowering Time and Northern Corn Leaf Blight (Setosphaeria turcica) Resistance in a Vast Commercial Maize Germplasm Set," BMC Plant Biology 12:56 (2012).

* cited by examiner

*Primary Examiner* — Li Zheng
(74) *Attorney, Agent, or Firm* — Dentons US LLP; Alissa Eagle

(57) ABSTRACT

The present disclosure provides maize plants exhibiting broad spectrum resistance to Northern Leaf Blight (NLB). Maize plants with multiple NLB resistance loci located in cis linkage on chromosome 8 are provided. Compositions, including novel polymorphic markers and methods for producing, breeding, identifying, and selecting plants or germplasm with a disease resistance phenotype are further provided.

23 Claims, 3 Drawing Sheets

Specification includes a Sequence Listing.

| DESIRED RECOMBINANTS | 5000 KERNELS | 10000 KERNELS | 20000 KERNELS | 30000 KERNELS | 50000 KERNELS |
|---|---|---|---|---|---|
| 1 | 0.9390 | 0.9960 | 1.0000 | 1.0000 | 1.0000 |
| 2 | 0.7690 | 0.9760 | 0.9998 | 1.0000 | 1.0000 |
| 3 | 0.5300 | 0.9170 | 0.9990 | 1.0000 | 1.0000 |
| 4 | 0.3080 | 0.8090 | 0.9958 | 1.0000 | 1.0000 |
| 5 | 0.1520 | 0.6570 | 0.9868 | 0.9998 | 1.0000 |
| 6 | 0.0649 | 0.4880 | 0.9666 | 0.9992 | 1.0000 |
| 7 | 0.0243 | 0.3290 | 0.9291 | 0.9976 | 1.0000 |
| 8 | 0.0081 | 0.2030 | 0.8690 | 0.9938 | 1.0000 |
| 9 | 0.0024 | 0.1140 | 0.7848 | 0.9858 | 1.0000 |
| 10 | 0.0007 | 0.0589 | 0.6802 | 0.9709 | 1.0000 |
| 11 | 0.0002 | 0.0281 | 0.5631 | 0.9459 | 0.9999 |
| 12 | 0.0000 | 0.0124 | 0.4439 | 0.9077 | 0.9998 |
| 13 | 0.0000 | 0.0051 | 0.3327 | 0.8542 | 0.9994 |
| 14 | 0.0000 | 0.0020 | 0.2369 | 0.7851 | 0.9987 |
| 15 | 0.0000 | 0.0007 | 0.1604 | 0.7022 | 0.9973 |
| 16 | 0.0000 | 0.0002 | 0.1032 | 0.6094 | 0.9945 |
| 17 | 0.0000 | 0.0001 | 0.0633 | 0.5120 | 0.9898 |
| 18 | 0.0000 | 0.0000 | 0.0370 | 0.4158 | 0.9820 |
| 19 | 0.0000 | 0.0000 | 0.0206 | 0.3261 | 0.9698 |
| 20 | 0.0000 | 0.0000 | 0.0110 | 0.2468 | 0.9519 |

FIG. 2

MAIZE PLANTS WITH IMPROVED DISEASE RESISTANCE

REFERENCE TO RELATED APPLICATION

This application is a continuation of U.S. patent application Ser. No. 16/145,987, filed Sep. 28, 2018, which claims the benefit of U.S. Provisional Application No. 62/566,305, filed on Sep. 29, 2017, each of which is incorporated herein by reference in its entirety.

INCORPORATION OF SEQUENCE LISTING

A sequence listing containing the file named "SEMB026US_ST25.txt" which is 8.0 kilobytes (measured in MS-Windows®) and created on Sep. 28, 2018, and comprises 20 sequences, and is incorporated herein by reference in its entirety.

FIELD OF THE INVENTION

The present invention relates to the field of plant breeding and more specifically to methods and compositions for producing maize plants exhibiting improved disease resistance and to a recombinant chromosomal segment for resistance.

BACKGROUND

Disease resistance is an important trait in agriculture, particularly for the production of food crops. Although disease resistance alleles have been identified in maize plants, efforts to combine several disease resistance traits in a single plant line have been hindered by tightly linked or even allelic loci conferring resistance to different pathogens. This is further complicated by high densities of repeated sequences in regions of plant genomes controlling disease resistance, which can greatly reduce the possibility of developing useful genetic markers. A need therefore remains for recombinant chromosomal segments and plants comprising such chromosomal segments for the heterozygous deployment of one or more of the resistance alleles.

SUMMARY

In an aspect, a recombinant chromosomal segment is provided to confer resistance to Northern Leaf Blight (NLB) in maize. The recombinant chromosomal segment comprises a first allele comprising an Ht2 locus and a second allele comprising an HtN locus, wherein said first allele and said second allele are in cis linkage on chromosome 8. In an aspect, the disclosure provides maize plants of a cultivated maize plant variety comprising the chromosomal segment that comprises a first allele comprising an Ht2 locus conferring NLB resistance and a second allele comprising an HtN locus conferring NLB resistance, wherein said first allele and said second allele are configured in cis linkage on chromosome 8. In some embodiments, said plant further comprises a third allele conferring NLB resistance, for example a locus selected from the group consisting of Ht1, Ht3, and HtM on chromosome 2. For example, said plant may further comprise an Ht1 locus on chromosome 2. In further embodiments, said chromosomal segment is flanked by marker loci Q-NZMAY009401770 (SEQ ID NO: 1) and Q-NZMAY009430172 (SEQ ID NO: 16) on chromosome 8. In yet further embodiments, said chromosomal segment is flanked by marker loci Q-ZMHt2 (SEQ ID NO: 6) and Q-NZMAY009238970 (SEQ ID NO: 11) on chromosome 8. Plants provided herein may comprise a recombinant chromosomal segment comprising an Ht2 locus from an NLB resistant parent plant, for example A619HT2, at a locus genetically linked to marker locus Q-NZMAY009401770 (SEQ ID NO: 1) or Q-ZMHt2 (SEQ ID NO: 6) on chromosome 8. Plants provided herein may also comprise a recombinant chromosomal segment comprising an HtN locus from an NLB resistant parent plant, for example B68HTN, at a locus genetically linked to marker locus Q-NZMAY009238970 (SEQ ID NO: 11) or Q-NZMAY009430172 (SEQ ID NO: 16) on chromosome 8. A619HT2 and B68HTN are dent corn inbreds available from the U.S. National Plant Germplasm System. In some embodiments, plants provided herein comprise a recombinant chromosomal segment comprising an Ht2 locus from an NLB resistant parent plant at marker locus Q-NZMAY009401770 (SEQ ID NO: 1) or Q-ZMHt2 (SEQ ID NO: 6) on chromosome 8 and a recombinant chromosomal segment comprising an HtN locus from an NLB resistant parent plant at marker locus Q-NZMAY009238970 (SEQ ID NO: 11) or Q-NZMAY009430172 (SEQ ID NO:16) on chromosome 8. For example, plants provided herein may comprise a recombinant chromosomal segment from A619HT2 at a locus genetically linked to marker locus Q-NZMAY009401770 (SEQ ID NO: 1) or Q-ZMHt2 (SEQ ID NO: 6) on chromosome 8 and a recombinant chromosomal segment from B68HTN at a locus genetically linked to marker locus Q-NZMAY009238970 (SEQ ID NO: 11) or Q-NZMAY009430172 (SEQ ID NO: 16) on chromosome 8. In certain embodiments, plants are provided wherein a representative sample of seed comprising said chromosomal segment has been deposited under Accession No. PTA-124466. In other embodiments, plants provided herein may be defined as inbred or hybrid plants. In further embodiments, plants provided herein may be of the subspecies *Zea mays* L. ssp. *indentata, Zea mays* L. ssp. *indurata*, or *Zea mays* L. ssp. *saccharata*. Plant parts of the plants provided herein are further described, including cells, seeds, roots, stems, leaves, ears, flowers, and pollen.

In another aspect, the invention provides a recombinant DNA segment comprising a first allele comprising an Ht2 locus and conferring NLB resistance and a second allele comprising an HtN locus and conferring NLB resistance. In certain embodiments, said first allele is derived from a plant of line A619HT2 and said second allele is derived from a plant of line B68HTN. In further embodiments, said chromosomal segment comprises a sequence selected from the group consisting of SEQ ID NOs: 2, 7, 12, and 12. In a further embodiment, said chromosomal segment is derived from the seed of the material identified as 17 9Y 1@ as deposited under ATCC Accession No. PTA-124466. Additional embodiments include said recombinant DNA segment comprised within a cell, seed, or plant. In yet further embodiments, said recombinant segment confers broad-spectrum resistance to NLB to said plant.

In another aspect, the instant disclosure provides methods for producing maize plants exhibiting broad-spectrum resistance to NLB, said method comprising: a) crossing a maize plant provided herein with itself or with a second maize plant of a different genotype to produce one or more progeny plants; and b) selecting a progeny plant comprising the chromosomal segments described herein. In some embodiments, selecting said progeny plant comprises marker-assisted selection. In further embodiments, marker-assisted selection comprises detecting at least one allele at a genomic locus flanked by marker loci Q-NZMAY009401770 (SEQ ID NO: 1) and Q-NZMAY009430172 (SEQ ID NO: 16) on chromosome 8. Marker-assisted selection may further comprise detecting at least one allele at a genomic locus flanked by marker loci Q-ZMHt2 (SEQ ID NO: 6) and Q-NZMAY009238970 (SEQ ID NO: 11) on chromosome 8. In further embodiments, marker-assisted selection comprises detecting at least one allele at a locus genetically linked to a marker locus selected from the group consisting of Q-NZMAY009401770 (SEQ ID NO: 1), Q-ZMHt2 (SEQ ID NO: 6), Q-NZMAY009238970 (SEQ ID NO: 11), and Q-NZMAY009430172 (SEQ ID NO: 16). For example, marker-assisted selection may comprise detecting at least one allele at a locus genetically linked to each of marker loci selected from the group consisting of Q-NZMAY009401770 (SEQ ID NO: 1) and Q-NZMAY009238970 (SEQ ID NO: 11). In embodiments of the methods described herein, the progeny plant is an $F_2$-$F_6$ progeny plant. Producing the progeny may comprise backcrossing, for example from 2-7 generations of backcrossing.

In another aspect, the invention provides a plant produced by the methods described herein, or a part of a plant produced by the methods described herein, such as a cell, a seed, a root, a stem, a leaf, an ear, a flower, and pollen.

BRIEF DESCRIPTION OF THE DRAWINGS

FIG. 2: Estimated probability of recovering n desired recombinants between Ht2 and HtN based on a theoretical local recombination rate of 2 Mb/cM.

DETAILED DESCRIPTION

Figure 1:
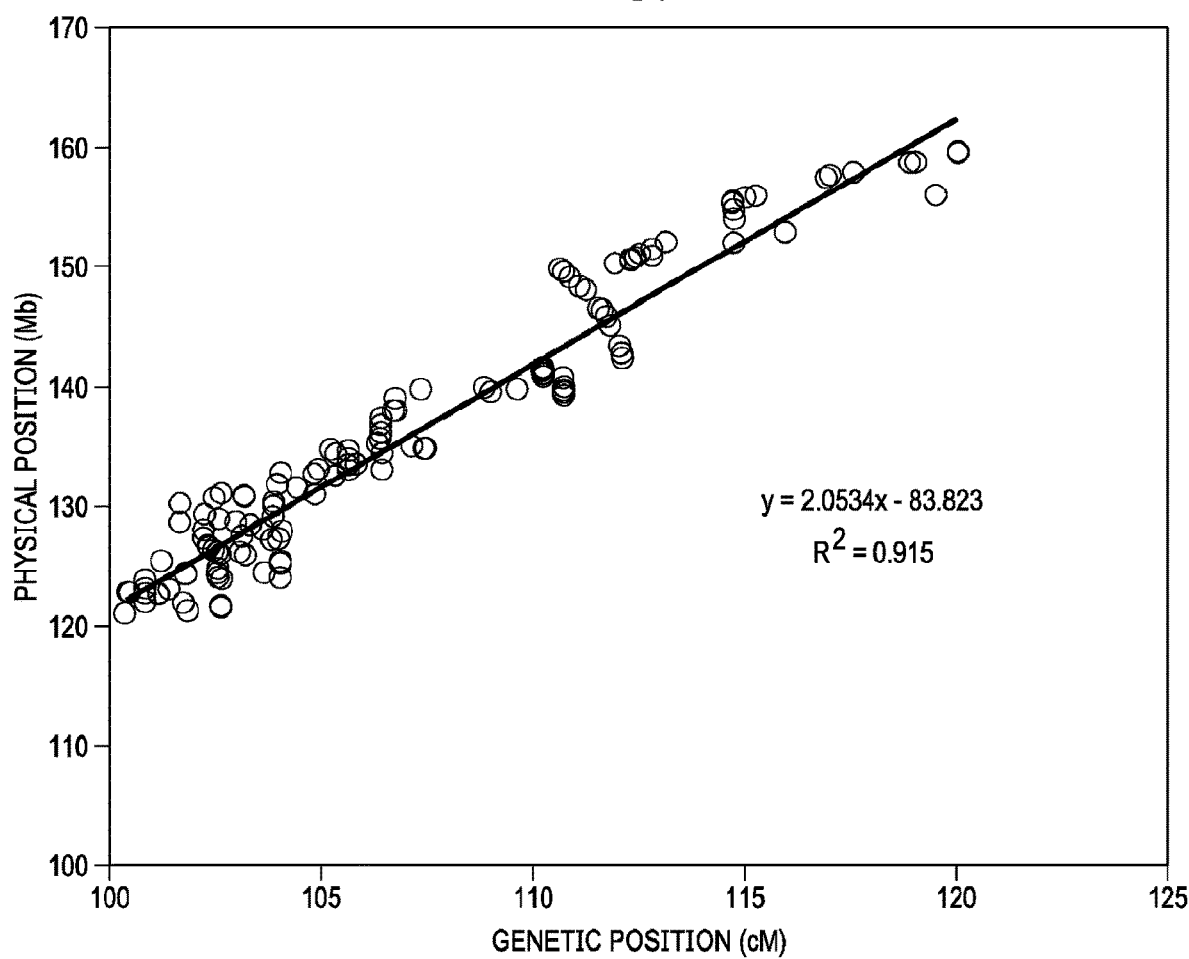
FIG. 1: Relationship between genetic and physical distance in the NLB_8.1 gene cluster on chromosome 8.

Northern Leaf Blight (NLB) is a foliar disease caused by *Exserohilum turcicum*, which is also known as *Setosphaeria turcica*, and results in yield losses in maize crops. Resistance to NLB in maize is conferred by both qualitative (monogenic) resistance and quantitative (polygenic) resistance. Qualitative genes for NLB resistance in maize that have been characterized are Ht1, Ht2, Ht3, HtN, and HtM. However, there are known isolates of NLB that can overcome each qualitative resistance gene. Ht2 and HtN are found in a NLB resistance gene cluster on chromosome 8. Efforts to combine various known disease resistance traits in a single plant line have been unsuccessful due to the tight linkage of these loci. In addition, the high density of repeated sequence in the NLB resistance gene cluster on chromosome 8 has made the development of genetic markers that could successfully assist in marker assisted breeding extremely difficult. Prior to the instant disclosure, resistance loci on chromosome 8 of the maize genome were believed to be so tightly linked that deployment of a favorable allele at a first locus could preclude deployment of a second favorable allele on the same chromosome. The tight linkage between these disease resistance loci is problematic because multiple alleles directed to different NLB isolates are needed to obtain broad spectrum NLB resistance. The inability to deploy multiple NLB resistance alleles directed to combinations of NLB isolates results in maize plants unacceptably susceptible to one or more NLB isolates.

Contrary to previous belief in the art that NLB resistance loci were so tightly linked as to be allelic, the present inventors have successfully produced a recombinant chromosomal segment comprising Ht2 and HtN NLB resistance alleles in a cis configuration on chromosome 8. This chromosomal segment is incorporated into maize plants to obtain broad spectrum resistance to NLB. The inventors have shown that these NLB resistance loci are not allelic, allowing for the stacking of these traits while simultaneously deploying additional favorable alleles. The invention also provides a recombinant chromosomal segment and maize plants comprising Ht2 and HtN NLB resistance alleles in a cis configuration. Methods of producing maize plants exhibiting broad spectrum resistance to NLB, as well as novel markers for tracking disease resistance alleles during plant breeding are further provided. The invention therefore represents a significant advance in the art by combining these disease resistance traits in plant lines capable of acting as donor parents for introgression of disease resistance into any desired maize genotype.

The invention additionally provides maize plants comprising Ht2 and HtN NLB resistance alleles in a cis configuration on chromosome 8, and further comprising additional NLB resistance alleles in trans, such that the plants exhibit broad spectrum resistance to NLB. In further embodiments, the invention provides maize plants comprising a recombinant chromosomal segment comprising an Ht2 locus from an NLB resistant parent plant at marker locus Q-NZMAY009401770 (SEQ ID NO: 1) or Q-ZMHt2 (SEQ ID NO: 6) on chromosome 8 and a recombinant chromosomal segment comprising an HtN locus from an NLB resistant parent plant at marker locus Q-NZMAY009238970 (SEQ ID NO: 11) or Q-NZMAY009430172 (SEQ ID NO: 16) on chromosome 8. The invention further provides a chromosomal segment and plants comprising NLB resistance alleles in a cis configuration as a result of a recombination event occurring between marker locus Q-NZMAY009401770 (SEQ ID NO: 1) and marker locus Q-NZMAY009430172 (SEQ ID NO: 16). In certain embodiments, maize plants of the invention comprise NLB resistance alleles in a cis configuration as a result of a recombination event occurring between marker locus Q-ZMHt2 (SEQ ID NO: 6) and marker locus Q-NZMAY009238970 (SEQ ID NO: 11).

The invention further provides a recombinant DNA segment comprising an Ht2 allele from a first genetic source and an HtN allele from a second genetic source. A recombinant chromosomal segment provided herein may comprise an Ht2 allele from a A619HT2 parent plant and an HtN allele from a B68HTN parent plant. In certain embodiments, a recombinant chromosomal segment is defined as comprising DNA from a first genetic source at marker locus Q-NZMAY009401770 (SEQ ID NO: 1) and DNA from a second genetic source at marker locus Q-NZMAY009430172 (SEQ ID NO: 16). In further embodiments, a recombinant chromosomal segment comprises DNA from a first genetic source at marker locus Q-ZMHt2 (SEQ ID NO: 6) and DNA from a second genetic source at marker locus Q-NZMAY009238970 (SEQ ID NO: 11) on chromosome 8. In a further embodiment, said chromosomal segment is derived from the seed of the material identified as 17 9Y 1@ as deposited under ATCC Accession No. PTA-124466. In another embodiment, a recombinant chromosomal segment provided by the invention confers broad-spectrum NLB resistance to a plant comprising the recombinant chromosomal segment. In one embodiment, the DNA segment is further defined as comprised within a cell. In another embodiment, the DNA segment is further defined as comprised within a seed. In yet another embodiment, the DNA segment is further defined as comprised within a plant.

The invention further provides novel trait-linked markers that can be used to produce, detect, or track plants comprising NLB resistance alleles during plant breeding. In particular embodiments, the invention provides the markers shown in Table 2, including markers within a genomic region flanked by markers Q-NZMAY009401770 (SEQ ID NO: 1) and Q-NZMAY009430172 (SEQ ID NO: 16). Other embodiments of the invention provide novel markers Q-NZMAY009401770 (SEQ ID NO: 1), Q-ZMHt2 (SEQ ID NO: 6), Q-NZMAY009238970 (SEQ ID NO: 11), and Q-NZMAY009430172 (SEQ ID NO: 16) which are useful in detection and tracking of plants comprising NLB resistance during plant breeding. Marker status for NLB resistance donors A619HT2 and B68HTN is shown in Table 3.

In other embodiments, the invention provides methods of producing maize plants comprising Ht2 and HtN NLB resistance alleles in a cis configuration on chromosome 8 by selecting or breeding plants having favorable alleles at markers within or genetically linked to the chromosomal segments disclosed herein. In some embodiments, the invention provides methods of selecting or breeding plants comprising detecting at least one allele at a locus within a genomic segment flanked by markers Q-NZMAY009401770 (SEQ ID NO: 1) and Q-NZMAY009430172 (SEQ ID NO: 16). In certain embodiments, the methods of the invention comprise detecting a marker within a genomic region flanked by marker loci Q-ZMHt2 (SEQ ID NO:6) and marker locus Q-NZMAY009238970 (SEQ ID NO: 11). In certain examples, plants may be selected by detecting one or more marker loci selected from the group consisting of Q-NZMAY009401770 (SEQ ID NO: 1), Q-ZMHt2 (SEQ ID NO: 6), Q-NZMAY009238970 (SEQ ID NO: 11), and Q-NZMAY009430172 (SEQ ID NO: 16).

I. Genomic Regions, Alleles, and Polymorphisms Associated with Disease Resistance in Maize Northern Leaf Blight (NLB) is a foliar disease caused by *Exserohilum turcicum*, also known as *Setosphaeria turcica*, which causes significant yield losses in maize crops. NLB resistance loci have been identified, including Ht1, Ht2, Ht3, HtN, and HtM. Both Ht2 and HtN reside in a NLB resistance gene cluster on chromosome 8 (NLB_8.1), while Ht1 resides on chromosome 2. Each of these genes confers resistance to certain NLB isolates (Table 1). In order to produce a maize plant with broad spectrum and durable resistance to NLB, several different resistance loci and alleles are combined in a single maize line. By combining the different loci the plant will have broad spectrum and durable resistance. The resistance is likely to be durable as it is unlikely that the pathogens will evolve to overcome the multiple modes of resistance. The recombinant chromosomal segments, plants and markers of the present invention provide the ability to stack multiple loci in a maize plant and overcome many of the obstacles in the art with respect to the stacking of resistance genes.

The Ht2 and HtN resistance loci in maize were previously believed to be so tightly linked that generation of recombination events between the two loci was not feasible. However, surprisingly, the present inventors have succeeded in producing plants comprising recombinant chromosomal intervals with Ht2 and HtN resistance alleles coupled in a cis configuration. Given the disclosure herein of the recombinant chromosomal segments and novel markers associated therewith, additional recombinant chromosomal segments could be generated using the methods and information described in the Examples. For instance, a cross between a maize plant comprising the HtN gene (such as B68HTN) and a plant comprising the HT2 gene (such as A619HT2) could be carried out, followed by selecting a progeny plant comprising a recombinant chromosomal segment using the markers provided herein. The estimated recombination rate and binomial sampling probabilities are used to determine the number of plants to generate. In certain examples, selection of progeny plants could be carried out by detecting at least one allele at a locus genetically linked to a marker locus selected from the group consisting of Q-NZMAY009401770 (SEQ ID NO: 1), Q-ZMHt2 (SEQ ID NO: 6), Q-NZMAY009238970 (SEQ ID NO: 11), and Q-NZMAY009430172 (SEQ ID NO: 16).

II. Introgression of Genomic Regions Associated with Disease Resistance

Marker-assisted introgression involves the transfer of a chromosomal region defined by one or more markers from a first genetic background to a second. Offspring of a cross that contain the introgressed genomic region can be identified by the combination of markers characteristic of the desired introgressed genomic region from a first genetic background and both linked and unlinked markers characteristic of the second genetic background.

The present invention provides novel accurate markers for identifying and tracking introgression of the newly provided recombinant chromosomal segments comprising NLB resistance loci disclosed herein into cultivated lines. In certain embodiments, the invention provides the markers set forth in Tables 2 and 3. Further embodiments of the invention provide novel markers Q-NZMAY009401770 (SEQ ID NO: 1), Q-ZMHt2 (SEQ ID NO: 6), Q-NZMAY009238970 (SEQ ID NO: 11), and Q-NZMAY009430172 (SEQ ID NO: 16), which can be useful in the identification or tracking of plants comprising broad spectrum NLB resistance, including plants comprising Ht2 and HtN NLB resistance alleles in a cis configuration on chromosome 8.

Markers within or linked to any of the genomic intervals of the present invention may be useful in a variety of breeding efforts that include introgression of genomic regions associated with disease resistance into a desired genetic background. For example, a marker within 40 cM, 20 cM, 15 cM, 10 cM, 5 cM, 2 cM, or 1 cM of a marker associated with disease resistance described herein can be used for marker-assisted introgression of genomic regions associated with a disease resistant phenotype.

Maize plants comprising one or more introgressed regions associated with a desired phenotype wherein at least 10%, 25%, 50%, 75%, 90%, or 99% of the remaining genomic sequences carry markers whose alleles match the recurrent parent genotype outside of the region targeted for disease resistance introgression are also provided. Maize plants comprising an introgressed region closely linked to, or adjacent to, the genomic regions and markers provided herein and associated with a disease resistance phenotype are also provided.

III. Development of Disease Resistant Maize Varieties

For most breeding objectives, commercial breeders work within germplasm that is "cultivated," "cultivated type" or "elite." As used herein, "elite" or "cultivated" variety means a variety that has resulted from breeding and selection for superior agronomic performance for use in agriculture. This includes the parents of a hybrid variety that may be cultivated, as well the variety that is itself cultivated. This germplasm is easier to breed because it generally performs well when evaluated for horticultural performance. A number of cultivated maize types have been developed which are agronomically elite and appropriate for commercial cultivation. However, the performance advantage a cultivated germplasm provides can be offset by a lack of allelic diversity. Breeders generally accept this tradeoff because progress is faster when working with cultivated material than when breeding with genetically diverse sources.

In contrast, when cultivated germplasm is crossed with non-cultivated germplasm, a breeder can gain access to novel alleles from the non-cultivated type. However, this approach can present significant difficulties due to fertility problems associated with crosses between diverse lines, and negative linkage drag from the non-cultivated parent. In maize plants, non-cultivated plant types can provide alleles associated with disease resistance. However, these non-cultivated types may have poor horticultural qualities such as vulnerability to certain deleterious traits or diseases.

A maize plant, as referenced herein, refers to any plant selected from the genus *Zea*, including, but not limited to, any plant selected from the species *Zea mays* L. In further embodiments, the plant may be selected from the subspecies *Zea mays* L. ssp. *mays*, for example *Zea mays* L. ssp. *indentata*, otherwise known as dent corn; *Zea mays* L. ssp. *indurata*, otherwise known as flint corn; *Zea mays* L. ssp. *saccharata*, otherwise known as sweet corn; *Zea mays* L. ssp. *amylacea*, otherwise known as flour corn; or *Zea mays* L. ssp. *everta*, otherwise known as popcorn. *Zea* plants include hybrids, inbreds, partial inbreds, or members of defined or undefined populations.

The process of introgress sing desirable resistance genes from non-cultivated lines into elite cultivated lines, while avoiding problems with linkage drag or low heritability, is a long and often arduous process. Success in deploying alleles derived from wild relatives therefore strongly depends on minimal or truncated introgressions that lack detrimental effects and reliable marker assays that replace phenotypic screens. Success is further defined by simplifying genetics for key attributes to allow focus on genetic gain for quantitative traits such as disease resistance. The process of introgression genomic regions from non-cultivated lines can be greatly facilitated by the availability of accurate markers for marker-assisted selection (MAS).

One of skill in the art would therefore understand that the alleles, polymorphisms, and markers provided by the invention allow the tracking and introduction of any of the genomic regions identified herein into any genetic background. In addition, the genomic regions associated with disease resistance disclosed herein can be introgressed from one genotype to another and tracked using MAS. Thus, Applicants' discovery of accurate markers associated with disease resistance facilitates the development of maize plants having beneficial phenotypes. For example, seed can be genotyped using the markers of the present invention in order to select for plants comprising desired genomic regions associated with disease resistance, without the need for growing plants to maturity to evaluate phenotype. Moreover, MAS allows identification of plants homozygous or heterozygous for a desired introgression.

Phenotypic evaluation of large populations is time-consuming, resource-intensive and not reproducible in every environment. Marker-assisted selection offers a feasible alternative. Molecular assays designed to detect unique polymorphisms, such as SNPs, are versatile. However, they may fail to discriminate alleles within and among maize species in a single assay. Structural rearrangements of chromosomes such as deletions impair hybridization and extension of synthetically labeled oligonucleotides. In the case of duplication events, multiple copies are amplified in a single reaction without distinction. The development and validation of accurate and highly predictive markers are therefore essential for successful MAS breeding programs.

A corn plant, seed, or cell provided herein can be genetically transformed. Numerous methods for plant transformation have been developed, including biological and physical plant transformation protocols. See, for example, Miki et al., "Procedures for Introducing Foreign DNA into Plants" in *Methods in Plant Molecular Biology and Biotechnology*, Glick and Thompson Eds., CRC Press, Inc., Boca Raton, pp. 67-88 (1993). In addition, expression vectors and in vitro culture methods for plant cell or tissue transformation and regeneration of plants are available. See, for example, Gruber et al., "Vectors for Plant Transformation," in *Methods in Plant Molecular Biology and Biotechnology*, Glick and Thompson Eds., CRC Press, Inc., Boca Raton, pp. 89-119 (1993).

One method for introducing an expression vector into plants is based on the natural transformation system of *Agrobacterium*. See, for example, Horsch et al., A Simple and General Method for Transferring Genes into Plants. Science, 227:1229-1231 (1985). *A. tumefaciens* and *A. rhizogenes* are plant pathogenic soil bacteria which genetically transform plant cells. Descriptions of *Agrobacterium* vector systems and methods for *Agrobacterium*-mediated gene transfer are provided by, for example, U.S. Pat. No. 5,563,055, incorporated herein by reference in its entirety.

Several methods of plant transformation, collectively referred to as direct gene transfer, have been developed as an alternative to *Agrobacterium*-mediated transformation. A generally applicable method of plant transformation is microprojectile-mediated transformation wherein DNA is carried on the surface of microprojectiles. The expression vector is introduced into plant tissues with a biolistic device that accelerates the microprojectiles to speeds of 300 to 600 m/s which is sufficient to penetrate plant cell walls and membranes.

Another method for physical delivery of DNA to plants is sonication of target cells. Alternatively, liposome and spheroplast fusion have been used to introduce expression vectors into plants. Electroporation of protoplasts and whole cells and tissues can also be used.

Following transformation of corn target tissues, expression of the above-described selectable marker genes allows for preferential selection of transformed cells, tissues, and/or plants, using regeneration and selection methods well-known in the art.

The foregoing methods for transformation would typically be used for producing a transgenic variety. The transgenic variety could then be crossed with another (non-transformed or transformed) variety, in order to produce a new transgenic variety. Alternatively, a genetic trait which has been engineered into a particular corn line using the foregoing transformation techniques could be moved into another line using traditional backcrossing techniques that are well-known in the plant breeding arts. For example, a backcrossing approach could be used to move an engineered trait from a public, non-elite variety into an elite variety, or from a variety containing a foreign gene in its genome into a variety or varieties which do not contain that gene.

Many desirable traits, such as those described here, that can be introduced through introgression or transformation can also be introduced directly into a plant by the use of genome-editing molecular techniques. One aspect of the invention includes plants with a genome that has been changed by site-specific genome modification techniques.

A corn plant, seed, or cell provided herein can also be produced by one or more genome engineering techniques or subject to further genomic editing. For example, one or more NLB resistance alleles can be introduced into an NLB susceptible background. Exemplary genome engineering techniques include meganucleases, zinc-finger nucleases, TALENs, and CRISPR/Cas9 systems. See, e.g., Gaj et al., ZFN, TALEN, and CRISPR/Cas-based methods for genome engineering. *Trends in Biotechnology*, 31:397-405 (2013). Additional genome engineering techniques known to those of ordinary skill in the art are also envisioned. Techniques of site-specific genome modification include the use of enzymes such as, endonucleases, recombinases, transposases, helicases and any combination thereof. In one aspect, an endonuclease is selected from a meganuclease, a zinc-finger nuclease (ZFN), a transcription activator-like effector nuclease (TALEN), an Argonaute, and an RNA-guided nuclease, such as a CRISPR associated nuclease. In another aspect, the endonuclease is Cas9 or Cpf1.

Site-specific genome modification enzymes induce a genome modification such as a double-stranded DNA break (DSB) or single-strand DNA break at the target site of a genomic sequence that is then repaired by the natural processes of homologous recombination (HR) or non-homologous end-joining (NHEJ). Sequence modifications then occur at the cleaved sites, which can include deletions or insertions that result in gene disruption in the case of NHEJ, or integration of exogenous sequences by homologous recombination. These techniques, for example, may be used to alter another locus in a plant containing the coupling event of this invention, to alter the coupling event of this invention or to re-create the coupling event of this invention in a different plant background.

IV. Molecular Assisted Breeding Techniques

Genetic markers that can be used in the practice of the present invention include, but are not limited to, restriction fragment length polymorphisms (RFLPs), amplified fragment length polymorphisms (AFLPs), simple sequence repeats (SSRs), simple sequence length polymorphisms (SSLPs), single nucleotide polymorphisms (SNPs), insertion/deletion polymorphisms (Indels), variable number tandem repeats (VNTRs), and random amplified polymorphic DNA (RAPD), isozymes, and other markers known to those skilled in the art. Marker discovery and development in crop plants provides the initial framework for applications to marker-assisted breeding activities (U.S. Patent Pub. Nos.: 2005/0204780, 2005/0216545, 2005/0218305, and 2006/00504538). The resulting "genetic map" is the representation of the relative position of characterized loci (polymorphic nucleic acid markers or any other locus for which alleles can be identified) to each other.

Polymorphisms comprising as little as a single nucleotide change can be assayed in a number of ways. For example, detection can be made by electrophoretic techniques including a single strand conformational polymorphism (Orita et al. (1989) *Genomics*, 8(2), 271-278), denaturing gradient gel electrophoresis (Myers (1985) *EPO* 0273085), or cleavage fragment length polymorphisms (Life Technologies, Inc., Gathersberg, MD), but the widespread availability of DNA sequencing often makes it easier to simply sequence amplified products directly. Once the polymorphic sequence difference is known, rapid assays can be designed for progeny testing, typically involving some version of PCR amplification of specific alleles (PASA; Sommer, et al., *Biotechniques* 12(1), 82-87, 1992), or PCR amplification of multiple specific alleles (PAMSA; Dutton and Sommer, *Biotechniques*, 11(6), 700-7002, 1991).

Polymorphic markers serve as useful tools for assaying plants for determining the degree of identity of lines or varieties (U.S. Pat. No. 6,207,367). These markers form the basis for determining associations with phenotypes and can be used to drive genetic gain. In certain embodiments of methods of the invention, polymorphic nucleic acids can be used to detect in a maize plant a genotype associated with disease resistance, identify a maize plant with a genotype associated with disease resistance, and to select a maize plant with a genotype associated with disease resistance. In certain embodiments of methods of the invention, polymorphic nucleic acids can be used to produce a maize plant that comprises in its genome an introgressed locus associated with disease resistance. In certain embodiments of the invention, polymorphic nucleic acids can be used to breed progeny maize plants comprising a locus associated with disease resistance.

Genetic markers may include "dominant" or "codominant" markers. "Codominant" markers reveal the presence of two or more alleles (two per diploid individual). "Dominant" markers reveal the presence of only a single allele. Markers are preferably inherited in codominant fashion so that the presence of both alleles at a diploid locus, or multiple alleles in triploid or tetraploid loci, are readily detectable, and they are free of environmental variation, i.e., their heritability is 1. A marker genotype typically comprises two marker alleles at each locus in a diploid organism. The marker allelic composition of each locus can be either homozygous or heterozygous. Homozygosity is a condition where both alleles at a locus are characterized by the same nucleotide sequence. Heterozygosity refers to different conditions of the allele at a locus.

Nucleic acid-based analyses for determining the presence or absence of the genetic polymorphism (i.e. for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with disease resistance in maize plants.

As used herein, nucleic acid analysis methods include, but are not limited to, PCR-based detection methods (for example, TaqMan assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) (Mullis et al. 1986 Cold Spring Harbor Symp. Quant. Biol. 51:263-273; European Patent 50,424; European Patent 84,796; European Patent 258,017; European Patent 237,362; European Patent 201,184; U.S. Pat. Nos. 4,683,202; 4,582,788; and 4,683,194), using primer pairs that are capable of hybridizing to the proximal sequences that define a polymorphism in its double-stranded form. Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613; 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252 all of which are incorporated herein by reference in their entirety. However, the compositions and methods of the present invention can be used in conjunction with any polymorphism typing method to type polymorphisms in genomic DNA samples. These genomic DNA samples used include but are not limited to, genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods, for example as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., *Genome Res.* 13:513-523, 2003); Cui et al., *Bioinformatics* 21:3852-3858, 2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. Typing of target sequences by microarray-based methods is disclosed in U.S. Pat. Nos. 6,799,122; 6,913,879; and 6,996,476.

Other methods for detecting SNPs and Indels include single base extension (SBE) methods. Examples of SBE methods include, but are not limited to, those disclosed in U.S. Pat. Nos. 6,004,744; 6,013,431; 5,595,890; 5,762,876; and 5,945,283.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, a locus or loci of interest can be directly sequenced using nucleic acid sequencing technologies. Methods for nucleic acid sequencing are known in the art and include technologies provided by 454 Life Sciences (Branford, CT), Agencourt Bioscience (Beverly, MA), Applied Biosystems (Foster City, CA), LI-COR Biosciences (Lincoln, NE), NimbleGen Systems (Madison, WI), Illumina (San Diego, CA), and VisiGen Biotechnologies (Houston, TX). Such nucleic acid sequencing technologies comprise formats such as parallel bead arrays, sequencing by ligation, capillary electrophoresis, electronic microchips, "biochips," microarrays, parallel microchips, and single-molecule arrays.

V. Additional Breeding Techniques

A corn plant or seed provided herein can also be subject to additional breeding using one or more known methods in the art, e.g., pedigree breeding, recurrent selection, mass selection, and mutation breeding. Pedigree breeding starts with the crossing of two genotypes, such as a corn variety comprising an NLB resistance QTL or NLB resistance allele or two coupled NLB resistance QTLs or two coupled NLB resistance alleles provided herein and another corn variety lacking such a locus. If the two original parents do not provide all the desired characteristics, other sources can be included in the breeding population. In the pedigree method, superior plants are selfed and selected in successive filial generations. In the succeeding filial generations the heterozygous condition gives way to homogeneous varieties as a result of self-fertilization and selection. Typically in the pedigree method of breeding, five or more successive filial generations of selfing and selection is practiced: $F_1$ to $F_2$; $F_2$ to $F_3$; $F_3$ to $F_4$; $F_4$ to $F_5$, etc. After a sufficient amount of inbreeding, successive filial generations will serve to increase seed of the developed variety. The developed variety can comprise homozygous alleles at about 95% or more of its loci.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, a corn variety can be crossed with another variety to produce a first generation progeny plant. The first generation progeny plant can then be backcrossed to one of its parent varieties to create a $BC_1$ or $BC_2$. Progenies are selfed and selected so that the newly developed variety has many of the attributes of the recurrent parent and yet several of the desired attributes of the non-recurrent parent. This approach leverages the value and strengths of the recurrent parent for use in new corn varieties.

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic line. A synthetic line is the resultant progeny formed by the intercrossing of several selected varieties.

Mass selection is another useful technique when used in conjunction with molecular marker enhanced selection. In mass selection, seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Also, instead of self-pollination, directed pollination could be used as part of the breeding program.

Mutation breeding can also be used to introduce new traits into a corn plant or seed provided herein. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, gamma rays (e.g., cobalt-60 or cesium-137), neutrons (product of nuclear fission by uranium-235 in an atomic reactor), beta radiation (emitted from radioisotopes such as phosphorus-32 or carbon-14), or ultraviolet radiation (from 2500 to 2900 nm)), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines). Transposon- or T-DNA-based mutagenesis is also encompassed by the present disclosure. Once a desired trait is observed through mutagenesis the trait can then be incorporated into existing germplasm by traditional breeding techniques.

VI. Deposit Information

A deposit of maize line 17 9Y 1 @, which is disclosed herein and referenced in the claims, was made with the American Type Culture Collection (ATCC), 10801 University Blvd., Manassas, VA 20110-2209. The date of deposit was Sep. 11, 2017, and the accession number for the deposited seeds is ATCC Accession No. PTA-124466. All restrictions upon the deposit have been removed, and the deposit is intended to meet all of the requirements of 37 C.F.R. § 1.801-1.809. The deposit will be maintained in the depository for a period of 30 years, or 5 years after the last request, or for the effective life of the patent, whichever is longer, and will be replaced if necessary during that period.

VII. Definitions

The following definitions are provided to better define the present invention and to guide those of ordinary skill in the art in the practice of the present invention. Unless otherwise noted, terms are to be understood according to conventional usage by those of ordinary skill in the relevant art.

As used herein, "Northern Leaf Blight" or "NLB", or "Northern Corn Leaf Blight" or "NCLB", refers to a plant disease caused by the fungal pathogen *Exserohilum turcicum*, which is also known as *Helminthosporium turcicum* and *Setosphaeria turcica*.

As used herein, the term "cis configuration" or "cis linkage" refers to an arrangement in which two or more alleles are linked on the same parental chromosome. The term "trans configuration" or "trans linkage" refers to a configuration in which two or more alleles are arranged on different parental chromosomes.

As used herein, the terms "recombinant" or "recombined" in the context of a chromosomal segment refer to recombinant DNA sequences comprising one or more genetic loci in a configuration in which they are not found in nature, for example as a result of a recombination event between homologous chromosomes during meiosis.

As used herein, the term "plant" includes plant cells, plant protoplasts, plant cells of tissue culture from which maize plants can be regenerated, plant calli, plant clumps and plant cells that are intact in plants or parts of plants such as pollen, flowers, seeds, leaves, stems, and the like.

As used herein, the term "population" means a genetically heterogeneous collection of plants that share a common parental derivation.

As used herein, the terms "variety" and "cultivar" mean a group of similar plants that by their genetic pedigrees and performance can be identified from other varieties within the same species.

As used herein, an "allele" refers to one of two or more alternative forms of a genomic sequence at a given locus on a chromosome.

A "Quantitative Trait Locus (QTL)" is a chromosomal location that encodes for at least a first allele that affects the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

As used herein, "elite" or "cultivated" variety means any variety that has resulted from breeding and selection for superior agronomic performance. The term "cultivated" in reference to a plant or variety includes the parent lines of a hybrid cultivated maize variety. An "elite plant" refers to a plant belonging to an elite variety. Numerous elite varieties are available and known to those of skill in the art of maize breeding. An "elite population" is an assortment of elite individuals or varieties that can be used to represent the state of the art in terms of agronomically superior genotypes of a given crop species, such as maize. Similarly, an "elite germplasm" or elite strain of germplasm is an agronomically superior germplasm.

As used herein, the term "introgressed," when used in reference to a genetic locus, refers to a genetic locus that has been introduced into a new genetic background, such as through backcrossing. Introgression of a genetic locus can be achieved through plant breeding methods and/or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion.

As used herein, "transgenic" means a plant or seed whose genome has been altered by the stable integration of recombinant DNA. A transgenic line includes a plant regenerated from an originally-transformed plant cell and progeny transgenic plants from later generations or crosses of a transformed plant.

As used herein, the term "linked" or "genetically linked," when used in the context of nucleic acid markers and/or genomic regions, means that the markers and/or genomic regions are located in proximity on the same linkage group or chromosome such that they tend to segregate together at meiosis.

As used herein, "resistance locus" means a locus associated with resistance or tolerance to disease. For instance, a resistance locus according to the present invention may, in certain embodiments, control resistance or susceptibility to NLB.

As used herein, "resistance allele" means the nucleic acid sequence associated with resistance or tolerance to disease.

As used herein "resistance" or "improved resistance" in a plant to disease conditions is an indication that the plant is more able to reduce disease burden than a non-resistant or less resistant plant. Resistance is a relative term, indicating that a "resistant" plant is more able to reduce disease burden compared to a different (less resistant) plant (e.g., a different plant variety) grown in similar disease conditions. One of skill will appreciate that plant resistance to disease conditions varies widely, and can represent a spectrum of more-resistant or less-resistant phenotypes. However, by simple observation, one of skill can generally determine the relative resistance of different plants, plant varieties, or plant families under disease conditions, and furthermore, will also recognize the phenotypic gradations of "resistant."

EXAMPLES

Example 1. Sources of Northern Leaf Blight Resistance

Resistance to Northern Leaf Blight (NLB) in maize is conferred by both qualitative (monogenic) resistance and quantitative (polygenic) resistance. Qualitative genes for NLB resistance in maize that have been well characterized are Ht1, Ht2, Ht3, HtN, and HtM. Both Ht2 and HtN reside in a NLB resistance gene cluster on chromosome 8 (NLB_8.1), while Ht1 resides on chromosome 2. There are known isolates of NLB that can overcome each of these qualitative resistance genes. The isolates are characterized into races by the resistance genes that they can overcome. Thus, races of NLB are characterized as Race 0, Race 1, Race 2, Race 3, Race N, Race M, and all possible permutations thereof (e.g. Race 12, Race 2N, etc), where the race number or letter indicates the Ht gene on which the isolate is virulent. Through multiple greenhouse assays, it was identified that stacking Ht1, Ht2 and HtN together in a hybrid should provide broad spectrum resistance against characterized races of NLB (Table 1).

TABLE 1

Summary of differential screens for NLB isolates and Ht gene stacks.

| Gene Combination | ET212 | ET210 | ET220 | 12EXS01 12EXS02 12EXS04 12EXS05 | 12EXS03 12EXS07 12EXS08 | 12EXS06 |
|---|---|---|---|---|---|---|
| Ht1 | S | R | R | S | S | S |
| Ht2 | S | S | R | R | R | R |
| HtN | R | S | S | S | R | S |
| Ht2 + HtN | R | S | R | R | R | R |
| Ht1 + Ht2 + HtN | R | R | R | R | R | R |

Example 2. Characterization of the NLB_8.1 Gene Cluster

Ht2 and HtN are very tightly linked, with physical distance of only about 113 kb between the genes. Given the relationship between physical to genetic distance ratio of approximately 2 Mb/cM surrounding the NLB_8.1 gene cluster (FIG. 1), the 113 kb between Ht2 and HtN is roughly equivalent to 0.05 cM. While Ht2 and HtN could be stacked in a trans configuration in a hybrid, this option requires independent selection on two traits and precludes deployment of other sources of resistance at the NLB_8.1 gene cluster.

Example 3. Coupling Ht2 and HtN Loci

In order to deploy the tightly linked Ht2 and HtN loci in a coupled configuration in an elite sweet corn background, a recombination event was first generated in a dent corn background to allow for genotyping using seed chipping. This would allow for introgression of Ht2 and HtN loci in a coupled configuration into elite sweet corn donors. A coupling event between Ht2 and HtN further allows for the two genes to be selected and deployed as a single trait, thus reducing phenotyping and marker genotyping efforts and allowing for simultaneous deployment of other desired traits. For this purpose, a cross between two dent corn inbreds, B68HTN (carrying the HtN gene) and A619HT2 (carrying the Ht2 gene), was carried out (B68HTN and A619HT2 available from the U.S. National Plant Germplasm System). F2 plants from the B68HTN/A619HT2 cross that were heterozygous for HtN and Ht2 were selected and selfed to produce a large population of F3 kernels.

Based on the estimated recombination rate around the NLB_8.1 region and binomial sampling probabilities, it was determined that it was necessary to create approximately 50,000 progeny to identify recombinants between HtN and Ht2 in the desired configuration (FIG. 2).

50,000 F3 kernels were subjected to seed chipping to identify putative recombinants between two upstream and two downstream flanking markers (Tables 2, 3). From these 50,000 chipped F3 kernels, 39 putative recombinants in the desired configuration were identified.

TABLE 2

Markers used to detect putative recombinants and targeted recombination events.

| | Marker Sequence (SEQ ID NO) | Probe 1 (SEQ ID NO) | Probe 2 (SEQ ID NO) | F Primer (SEQ ID NO) | R Primer (SEQ ID NO) | SNP | SNP Position | Favorable Allele |
|---|---|---|---|---|---|---|---|---|
| Q-NZMAY009401770 | 1 | 2 | 3 | 4 | 5 | [C/T] | 74 | C |
| Q-ZMHt2 | 6 | 7 | 8 | 9 | 10 | [T/G] | 34 | T |
| Q-NZMAY009238970 | 11 | 12 | 13 | 14 | 15 | [C/T] | 75 | C |
| Q-NZMAY009430172 | 16 | 17 | 18 | 19 | 20 | [C/T] | 90 | C |

TABLE 3

Identification of putative recombinants.

| Marker | Physical Position | Favorable alleles | A619HT2 | | B68HTN | | Target recombinant 1 | | Target recombinant 2 | |
|---|---|---|---|---|---|---|---|---|---|---|
| Q-NZMAY009401770 | 152,245,739 | C | C | C | T | T | C | C | C | T |
| Q-ZMHt2 | 152,245,836 | T | T | T | G | G | T | T | T | G |
| Q-NZMAY009238970 | 152,358,289 | C | T | T | C | C | C | T | C | C |
| Q-NZMAY009430172 | 152,379,449 | C | T | T | C | C | C | T | C | C |

Example 4. Validation of Putative Ht2/HtN Recombination Events by Genotyping

Putative recombinants were sown, sampled for leaf tissue and subjected to two rounds of genotypic validation using the same set of TaqMan markers. The targeted recombination event between Ht2 and HtN was validated genotypically in only four of the 39 putative recombinants (Table 4). These 4 recombinants were selfed to obtain F4 ears. F4 seed was obtained from two of the events ("Event 0009" and "Event 0299"), and inventories from these 2 putative recombinants were planted to self and obtain F5 ears from fixed recombinants.

TABLE 4

F3 genotypes for plants in which the targeted recombination event was validated.

| Marker | Physical Position | Favorable alleles | Event 0009 | | Event 0037 | | Event 0255 | | Event 0299 | |
|---|---|---|---|---|---|---|---|---|---|---|
| Q-NZMAY009401770 | 152,245,739 | C | C | C | C | C | C | T | C | C |
| Q-ZMHt2 | 152,245,836 | T | T | T | T | T | T | G | T | T |
| Q-NZMAY009238970 | 152,358,289 | C | C | T | C | T | C | C | C | T |
| Q-NZMAY009430172 | 152,379,449 | C | C | T | C | T | C | C | C | T |

Example 5. Validation of Putative Ht2/HtN Recombination Events by Phenotyping The two putative independent recombination events between Ht2 and HtN ("Event 0009" and "Event 0299") were recovered in the F3 generation after chipping 50,000 kernels from heterozygous F2 plants and validated phenotypically as F5 lines using Race 2 and Race N isolates.

The two F3 recombinants were used to derive F5 lines fixed for the putative Ht2-HtN coupling events. F4 plants were genotyped across the trait region from 152,245,739 to 152,379,449 bp (Table 5), and plants that were fixed across the trait region were selfed to develop F5 lines.

TABLE 5

Genotypes of parental lines and selected F4 recombinants.

| Marker | Trait Linkage | Physical Position | A619HT2 | B68HTN | Event 0009 [F4] | Event 0299 [F4] |
|---|---|---|---|---|---|---|
| Q-NZMAY009401770 | Ht2 | 152,245,739 | CC | TT | CC | CC |
| Q-ZMHt2 | Ht2 | 152,245,836 | TT | GG | TT | TT |
| Q-NZMAY009238970 | HtN | 152,358,289 | TT | CC | CC | CC |
| Q-NZMAY009430172 | HtN | 152,379,449 | TT | CC | CC | CC |

Two of these F5 lines were used along with parental checks for phenotypic validation of the coupling event. The specific entries used for phenotypic validation were: A619 (Female parent isoline without Ht2); A619Ht2 (Female parent line); B68 (Male parent isoline without HtN); B68HtN (Male parent line); Event 0009; Event 0229.

These entries were planted in two greenhouse experiments. Each experiment was planted as a randomized complete block design with 2 replications. The first experiment was inoculated with a Race 2 isolate (Et212) of Northern Leaf Blight (NLB). The second experiment was inoculated with a Race N (Et234) isolate of NLB. The race type of these isolates was determined based on prior testing on differential panels as well as the reactions on the parental lines. The two experiments were conducted separately to avoid cross contamination with the two isolates.

Figure 3:
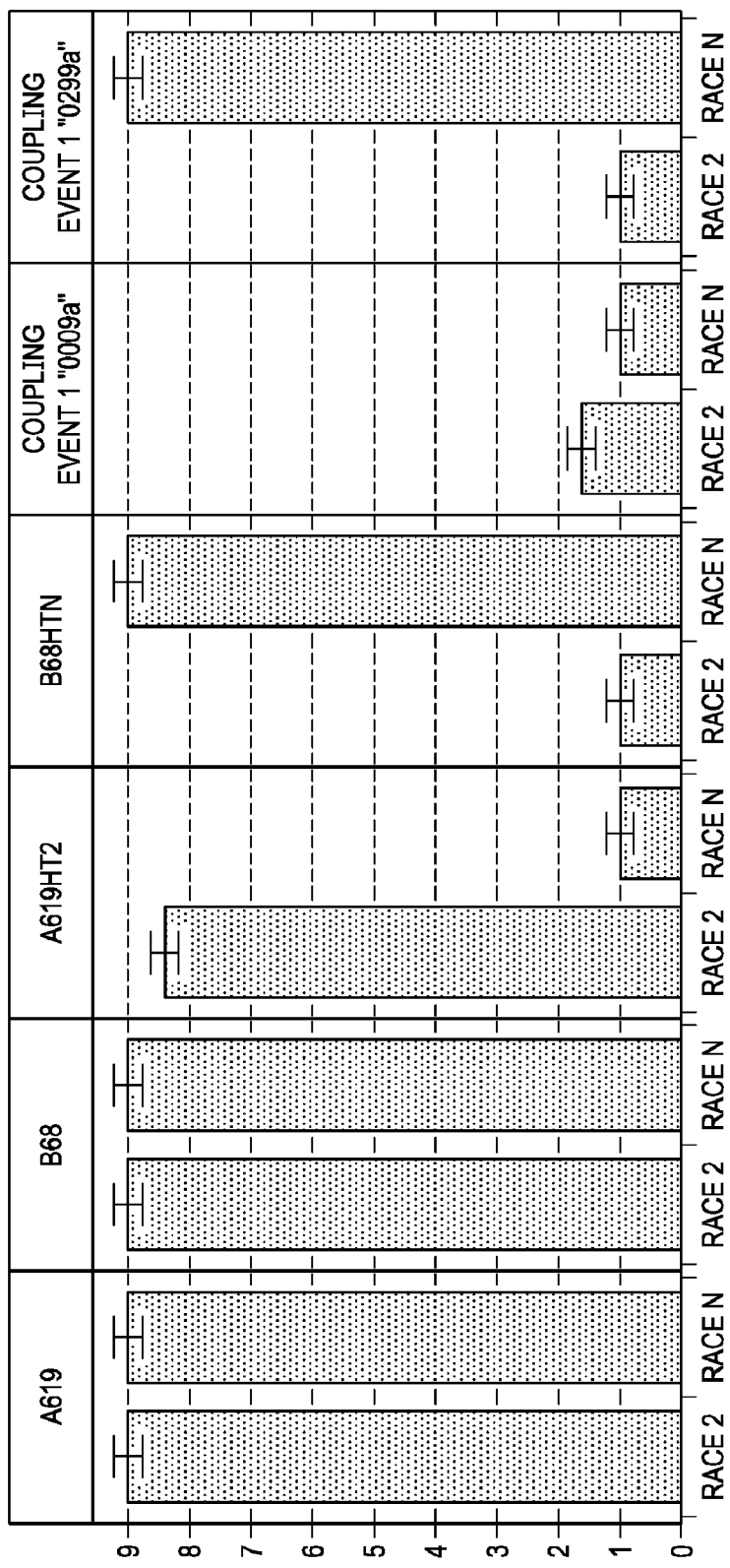
FIG. 3: Results of validation experiments with Race 2 and Race N isolates.

Results from the Race 2 and Race N experiments are shown in FIG. 3. For the Race 2 experiment, A619, B68, and A619Ht2 were all susceptible to the Race 2 isolate, while B68HtN was resistant as expected. Both Event 0009 and Event 0299 were resistant to the Race 2 isolate and showed the same "flecking" type resistant reaction (pinpoint lesions) as B68HtN. Therefore, both Event 0009 and Event 0299 carry the resistant HtN allele from B68HtN. For the Race N experiment, A619, B68, and B68HtN were susceptible, while A619Ht2 was resistant as expected. Event 0009 was resistant to the Race N isolate, while Event 0299 was susceptible. Event 0009 showed the same chlorotic lesion type reaction as A619Ht2, while Event 0299 showed large susceptible type lesions. Therefore, Event 0009 inherited the resistant Ht2 allele from A619Ht2, while Event 0299 carries the susceptible allele from B68HtN. These results demonstrate that the resistant alleles at the Ht2 and HtN loci have been successfully coupled in the fixed Event 0009.

Example 6. Introgression of Ht2/HtN Recombination Events

One putative recombinant between Ht2 and HtN, "Event 0009", is validated, demonstrating that Ht2 and HtN have been linked in the coupling configuration. The line "Event 0009" underwent 4 generations of selfing and was designated "17 9Y 1 @". The coupled Ht2 and HtN loci in dent line 17 9Y 1 @ may be introgressed into elite sweet corn inbreds or any other Zea mays L. ssp. The coupling event is identified unambiguously in breeding germplasm and selected for in segregating breeding populations using a combination of one marker associated with Ht2 upstream of the recombination breakpoint (e.g. Q-NZMAY009401770), and a second marker associated with HtN downstream of the recombination breakpoint (e.g. Q-NZMAY009238970). This strategy can distinguish plants carrying the coupling event from plants carrying HtN alone, plants carrying Ht2 alone, or plants carrying no resistant alleles.

What is claimed is:

1. A maize plant of a cultivated maize plant variety comprising a recombinant chromosomal segment that comprises a first allele at the Ht2 locus that confers resistance to NLB and a second allele at the HtN locus that confers resistance to NLB, wherein said recombinant chromosomal segment is flanked in the genome of said plant by marker locus Q-NZMAY009401770 (SEQ ID NO: 1) and marker locus Q-NZMAY009430172 (SEQ ID NO: 16) on chromosome 8, wherein said first allele comprises marker locus Q-NZMAY009401770 (SEQ ID NO: 1) or marker locus Q-ZMHt2 (SEQ ID NO: 6) and wherein said second allele comprises marker locus Q-NZMAY009238970 (SEQ ID NO: 11) or marker locus Q-NZMAY009430172 (SEQ ID NO: 16), and wherein said first allele and said second allele are configured in cis linkage on said chromosomal segment.

2. The maize plant of claim 1, wherein said plant further comprises a third allele conferring NLB resistance.

3. The maize plant of claim 2, wherein said third allele conferring NLB resistance comprises
   a) a locus selected from the group consisting of Ht1, Ht3, and HtM; or
   b) an Ht1 locus on chromosome 2.

4. The maize plant of claim 1, wherein said recombinant chromosomal segment is flanked by marker loci Q-ZMHt2 (SEQ ID NO: 6) and Q-NZMAY009238970 (SEQ ID NO: 11) on chromosome 8.

5. The maize plant of claim 1, wherein said plant comprises a recombinant chromosomal segment comprising
   a) an Ht2 locus from an NLB resistant parent plant at marker locus Q-NZMAY009401770 (SEQ ID NO: 1) or Q-ZMHt2 (SEQ ID NO: 6) and an HtN locus from an NLB resistant parent plant at marker locus Q-NZMAY009238970 (SEQ ID NO: 11) or Q-NZMAY009430172 (SEQ ID NO:16) on chromosome 8; or
   b) an Ht2 locus from A619HT2 at a locus genetically linked to marker locus Q-NZMAY009401770 (SEQ ID NO: 1) or Q-ZMHt2 (SEQ ID NO: 6) and an HtN locus from B68HTN at a locus genetically linked to marker locus Q-NZMAY009238970 (SEQ ID NO: 11) or Q-NZMAY009430172 (SEQ ID NO: 16) on chromosome 8.

6. The maize plant of claim 5, wherein said NLB resistant parent is A619HT2 or B68HTN.

7. The maize plant of claim 1, wherein a representative sample of seed comprising said chromosomal segment has been deposited under Accession No. PTA-124466.

8. The maize plant of claim 1, defined as an inbred or hybrid plant.

9. A plant part of the maize plant of claim 1, wherein the plant part comprises the recombinant chromosomal segment.

10. The plant part of claim 9, wherein the plant part is a cell, a seed, a root, a stem, a leaf, an ear, a flower, or pollen.

11. The maize plant of claim 1, wherein said plant is of the subspecies *Zea mays* L. ssp. *indentata, Zea mays* L. ssp. *indurata*, or *Zea mays* L. ssp. *saccharata*.

12. A recombinant DNA segment comprising a first allele at the Ht2 locus that confers resistance to NLB and a second allele at the HtN locus that confers resistance to NLB, wherein said first allele comprises marker locus Q-NZMAY009401770 (SEQ ID NO: 1) or marker locus Q-ZMHt2 (SEQ ID NO: 6) on chromosome 8 and wherein said second allele comprises marker locus Q-NZMAY009238970 (SEQ ID NO: 11) or marker locus Q-NZMAY009430172 (SEQ ID NO: 16) on chromosome 8, wherein said first allele and said second allele are configured in cis linkage on said chromosomal segment, and wherein a representative sample of seed comprising said first allele and said second allele has been deposited under ATCC Accession No. PTA-124466.

13. The recombinant DNA segment of claim 12, wherein
   a) said first allele is derived from a plant of line A619HT2 and said second allele is derived from a plant of line B68HTN; or
   b) said chromosomal segment comprises a sequence selected from the group consisting of SEQ ID NOs: 2, 7, 12, and 17.

14. The recombinant DNA segment of claim 12, further defined as comprised within a cell, a seed, or a plant.

15. The recombinant DNA segment of claim 14, wherein said DNA segment confers broad-spectrum resistance to NLB to said plant.

16. A maize plant, cell, or seed comprising the recombinant DNA segment of claim 12, wherein a representative sample of seed comprising said recombinant DNA segment has been deposited under ATCC Accession No. PTA-124466.

17. A method for producing a maize plant exhibiting broad-spectrum resistance to NLB, said method comprising:
   a) crossing the maize plant of claim 1 with itself or with a second maize plant of a different genotype to produce one or more progeny plants; and
   b) selecting a progeny plant comprising said recombinant chromosomal segment.

18. The method of claim 17, wherein selecting said progeny plant comprises marker-assisted selection.

19. The method of claim 18, wherein said marker-assisted selection comprises
   a) detecting at least one allele at a genomic locus flanked by marker loci Q-NZMAY009401770 (SEQ ID NO: 1) and Q-NZMAY009430172 (SEQ ID NO: 16) on chromosome 8;
   b) detecting at least one allele at a genomic locus flanked by marker loci Q-ZMHt2 (SEQ ID NO: 6) and Q-NZMAY009238970 (SEQ ID NO: 11) on chromosome 8;

c) detecting at least one allele at a locus genetically linked to a marker locus selected from the group consisting of Q-NZMAY009401770 (SEQ ID NO: 1), Q-ZMHt2 (SEQ ID NO: 6), Q-NZMAY009238970 (SEQ ID NO: 11), and Q-NZMAY009430172 (SEQ ID NO: 16); or d) detecting at least one allele at a locus genetically linked to each of marker loci selected from the group consisting of Q-NZMAY009401770 (SEQ ID NO: 1) and Q-NZMAY009238970 (SEQ ID NO: 11).

20. The method of claim 17, wherein the progeny plant is an F2-F6 progeny plant.

21. The method of claim 17, wherein producing the progeny plant comprises backcrossing.

22. The method of claim 21, wherein backcrossing comprises from 2-7 generations of backcrossing.

23. A plant or a part thereof, produced by the method of claim 17, wherein the plant or a part thereof comprises the recombinant chromosomal segment.

* * * * *

SEQUENCE LISTING

```
<160> NUMBER OF SEQ ID NOS: 20

<210> SEQ ID NO 1
<211> LENGTH: 160
<212> TYPE: DNA
<213> ORGANISM: Zea mays
<220> FEATURE:
<221> NAME/KEY: misc_feature
<222> LOCATION: (83)..(83)
<223> OTHER INFORMATION: n is a, c, g, or t

<400> SEQUENCE: 1
actctctcag gcttagctcc tcgctgaaca tggcgtcggt gggcttcttc ccagtgacga      60
cttcgagaag catcaccccg tanctgaaaa cgtcgctctt ccttgacgct ttaccggttg     120
aagcgtactc tgtagtaatt aatgtcagtt cacggcgaag                           160

<210> SEQ ID NO 2
<211> LENGTH: 18
<212> TYPE: DNA
<213> ORGANISM: Artificial sequence
<220> FEATURE:
<223> OTHER INFORMATION: Probe

<400> SEQUENCE: 2
```

-continued tcgagaagca tcaccccg                                            18

<210> SEQ ID NO 3
<211> LENGTH: 18
<212> TYPE: DNA
<213> ORGANISM: Artificial sequence
<220> FEATURE:
<223> OTHER INFORMATION: Probe

<400> SEQUENCE: 3
tcgagaagca ttaccccg                                            18

<210> SEQ ID NO 4
<211> LENGTH: 17
<212> TYPE: DNA
<213> ORGANISM: Artificial sequence
<220> FEATURE:
<223> OTHER INFORMATION: Primer

<400> SEQUENCE: 4
gcgtcggtgg gcttctt                                             17

<210> SEQ ID NO 5
<211> LENGTH: 22
<212> TYPE: DNA
<213> ORGANISM: Artificial sequence
<220> FEATURE:
<223> OTHER INFORMATION: Primer

<400> SEQUENCE: 5
caaggaagag cgacgttttc ag                                       22

<210> SEQ ID NO 6
<211> LENGTH: 61
<212> TYPE: DNA
<213> ORGANISM: Zea mays

<400> SEQUENCE: 6
gaggagctaa gcctgagaga gtgggtcagg caggctattc catcaggact cgctcatgtc    60
g                                                                   61

<210> SEQ ID NO 7
<211> LENGTH: 16
<212> TYPE: DNA
<213> ORGANISM: Artificial sequence
<220> FEATURE:
<223> OTHER INFORMATION: Probe

<400> SEQUENCE: 7
tcaggcagtc tattcc                                              16

<210> SEQ ID NO 8
<211> LENGTH: 14
<212> TYPE: DNA
<213> ORGANISM: Artificial sequence
<220> FEATURE:
<223> OTHER INFORMATION: Probe

<400> SEQUENCE: 8
aggcaggcta ttcc                                                14

<210> SEQ ID NO 9
<211> LENGTH: 22
<212> TYPE: DNA
<213> ORGANISM: Artificial sequence

```
<220> FEATURE:
<223> OTHER INFORMATION: Primer

<400> SEQUENCE: 9
gaggagctaa gcctgagaga gt                                            22

<210> SEQ ID NO 10
<211> LENGTH: 20
<212> TYPE: DNA
<213> ORGANISM: Artificial sequence
<220> FEATURE:
<223> OTHER INFORMATION: Primer

<400> SEQUENCE: 10
cgacatgagc gagtcctgat                                               20

<210> SEQ ID NO 11
<211> LENGTH: 154
<212> TYPE: DNA
<213> ORGANISM: Zea mays
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t

<400> SEQUENCE: 11
ggttgtttcc actaagagac agtactgata agctggtaag gttagcaaat gtaccaggga    60
tgcttccatt gatgctgttg ttacctgctt gnaaantttc taggagcgtg ctatggtttc   120
caattgaagt tggtagcatc cctgtgaact catt                               154

<210> SEQ ID NO 12
<211> LENGTH: 19
<212> TYPE: DNA
<213> ORGANISM: Artificial sequence
<220> FEATURE:
<223> OTHER INFORMATION: Probe

<400> SEQUENCE: 12
caggtaacaa cagcatcaa                                                19

<210> SEQ ID NO 13
<211> LENGTH: 18
<212> TYPE: DNA
<213> ORGANISM: Artificial sequence
<220> FEATURE:
<223> OTHER INFORMATION: Probe

<400> SEQUENCE: 13
aggtaacaac aacatcaa                                                 18

<210> SEQ ID NO 14
<211> LENGTH: 23
<212> TYPE: DNA
<213> ORGANISM: Artificial sequence
<220> FEATURE:
<223> OTHER INFORMATION: Primer

<400> SEQUENCE: 14
caaatgtacc agggatgctt cca                                           23

<210> SEQ ID NO 15
```

```
<211> LENGTH: 24
<212> TYPE: DNA
<213> ORGANISM: Artificial sequence
<220> FEATURE:
<223> OTHER INFORMATION: Primer

<400> SEQUENCE: 15
gaaaccatag cacgctccta gaaa                                              24

<210> SEQ ID NO 16
<211> LENGTH: 193
<212> TYPE: DNA
<213> ORGANISM: Zea mays
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (57)..(58)
<223> OTHER INFORMATION: n is a, c, g, or t
<220> FEATURE:
<221> NAME/KEY: misc_feature
<222> LOCATION: (110)..(110)
<223> OTHER INFORMATION: n is a, c, g, or t
<220> FEATURE:
<221> NAME/KEY: misc_feature
<222> LOCATION: (188)..(188)
<223> OTHER INFORMATION: n is a, c, g, or t

<400> SEQUENCE: 16
gtttatctcc gccttaagag gtagntgttc tggtgctcgg ttgcgtagca gtaaagnnag        60
ttttcgtcgt gatgctgcta ttactgaacc gggaggtatg cgacttctan gagtagttgc       120
ttattagcct acagaaaata tagggatctg gagactggtt atgtttcatg gctgttcttc       180
tttcaccngt acc                                                          193

<210> SEQ ID NO 17
<211> LENGTH: 17
<212> TYPE: DNA
<213> ORGANISM: Artificial sequence
<220> FEATURE:
<223> OTHER INFORMATION: Probe

<400> SEQUENCE: 17
catacctccc ggttcag                                                      17

<210> SEQ ID NO 18
<211> LENGTH: 17
<212> TYPE: DNA
<213> ORGANISM: Artificial sequence
<220> FEATURE:
<223> OTHER INFORMATION: Probe

<400> SEQUENCE: 18
catacctccc agttcag                                                      17

<210> SEQ ID NO 19
<211> LENGTH: 25
<212> TYPE: DNA
<213> ORGANISM: Artificial sequence
<220> FEATURE:
<223> OTHER INFORMATION: Primer

<400> SEQUENCE: 19
agttttcgtc gtgatgctgc tatta                                             25
```

```
<210> SEQ ID NO 20
<211> LENGTH: 29
<212> TYPE: DNA
<213> ORGANISM: Artificial sequence
<220> FEATURE:
<223> OTHER INFORMATION: Primer

<400> SEQUENCE: 20
ccagtctcca gatccctata ttttctgta                                      29
```